United States Patent
Man et al.

(10) Patent No.: US 9,347,896 B2
(45) Date of Patent: May 24, 2016

(54) CROSS-SECTION PROCESSING-AND-OBSERVATION METHOD AND CROSS-SECTION PROCESSING-AND-OBSERVATION APPARATUS

(71) Applicant: HITACHI HIGH-TECH SCIENCE CORPORATION, Minato-ku, Tokyo (JP)

(72) Inventors: Xin Man, Tokyo (JP); Tatsuya Asahata, Tokyo (JP); Atsushi Uemoto, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 0 days.

(21) Appl. No.: 14/475,046

(22) Filed: Sep. 2, 2014

(65) Prior Publication Data
US 2015/0060664 A1 Mar. 5, 2015

(30) Foreign Application Priority Data
Sep. 3, 2013 (JP) .................................. 2013-182586

(51) Int. Cl.
*G01N 23/225* (2006.01)
*H01J 37/28* (2006.01)
*H01J 37/305* (2006.01)
(Continued)

(52) U.S. Cl.
CPC ...... *G01N 23/2202* (2013.01); *G01N 23/20091* (2013.01); *G01N 23/2251* (2013.01); *H01J 37/28* (2013.01); *H01J 37/3056* (2013.01); *G01N 1/32* (2013.01); *G01N 2223/418* (2013.01); *H01J 2237/2811* (2013.01); *H01J 2237/31749* (2013.01)

(58) Field of Classification Search
CPC . G01N 23/20091; H01J 37/28; H01J 37/3056
See application file for complete search history.

(56) References Cited

U.S. PATENT DOCUMENTS

| | | | | |
|---|---|---|---|---|
| 5,952,658 A | * | 9/1999 | Shimase | H01J 37/304 250/492.21 |
| 2008/0293832 A1 | * | 11/2008 | Yokoi | G01N 1/42 516/98 |

(Continued)

FOREIGN PATENT DOCUMENTS

| | | | | |
|---|---|---|---|---|
| JP | 2008270073 | | 11/2008 | |
| WO | WO 2012/169323 A1 | * | 12/2012 | H01J 37/317 |

*Primary Examiner* — Phillip A Johnston
*Assistant Examiner* — Eliza Osenbaugh-Stewar
(74) *Attorney, Agent, or Firm* — Adams & Wilks

(57) ABSTRACT

A cross-section processing-and-observation method, including a cross-section exposure step in which a sample is irradiated with a focused ion beam to expose a cross-section of the sample, and a cross-sectional image acquisition step in which the cross-section is irradiated with an electron beam to acquire a cross-sectional image of the cross-section. The cross-section exposure step and the cross-sectional image acquisition step are repeatedly performed along a predetermined direction of the sample at a setting interval to acquire multiple cross-sectional images of the sample. The method also includes a specific observation target detection step in which a predetermined specific observation target from the cross-sectional image acquired a the cross-sectional image acquisition step is detected. In the specific observation target detection step, after a predetermined specific observation target is detected, the setting interval of the cross-section exposure step is set to be shorter than that before the specific observation target is detected.

13 Claims, 10 Drawing Sheets

(51) Int. Cl.
*G01N 23/22* (2006.01)
*G01N 23/20* (2006.01)
*G01N 1/32* (2006.01)

(56) References Cited

U.S. PATENT DOCUMENTS

2009/0283677 A1* 11/2009 Ikku .................. G01N 23/2208
                                                    250/307
2010/0032302 A1* 2/2010 Holtermann ........ H01J 37/3056
                                                    205/81
2010/0072365 A1* 3/2010 Shoham et al. ................ 250/307
2014/0076717 A1* 3/2014 Nanri .................... H01J 37/244
                                                    204/192.33
2014/0226003 A1* 8/2014 Phaneuf ................ H01J 37/222
                                                    348/80

* cited by examiner

CROSS-SECTION PROCESSING-AND-OBSERVATION METHOD AND CROSS-SECTION PROCESSING-AND-OBSERVATION APPARATUS

CROSS REFERENCE TO RELATED APPLICATION

This application is based upon and claims the benefit of priority of Japanese Patent Application No. 2013-182586 filed on Sep. 3, 2013, the contents of which are incorporated herein by reference in its entirety.

BACKGROUND OF THE INVENTION

Field of the Invention

The present invention relates to a cross-section processing-and-observation method and a cross-section processing-and-observation apparatus, in which a cross-section of a sample, which is formed by a focused ion beam, is irradiated with an electron beam to obtain a cross-sectional image of the sample.

For example, as a method of analyzing an internal structure of a sample such as a semiconductor device or performing a three-dimensional observation thereof, a cross-section processing-and-observation method is known, the method including: scanning an electron beam (EB) using a scanning electron microscope (SEM) to acquire plural cross-sectional images of the sample while repeatedly performing cross-section processing (etching processing) using a focused ion beam (FIB); and combining the plural cross-sectional images to construct a three-dimensional image of the sample (for example, JP-A-2008-270073).

This cross-section processing-and-observation method is a method called "Cut&See" in which a composite charged particle beam device is used, and has an advantageous effect compared to other methods in that a cross-sectional image of a sample can be seen and the inside of the sample can be three-dimensionally observed from various directions.

As a specific example, a sample is irradiated with an FIB to etch the sample such that a cross-section of the sample is exposed. Next, the exposed cross-section is observed with a SEM to acquire a cross-sectional image. Next, the sample is etched again to expose the next cross-section, and a second cross-sectional image is acquired by the SEM observation. By repeating the etching processing and the SEM observation in this way along an arbitrary direction of the sample, plural cross-sectional images are acquired. Lastly, by combining the acquired plural cross-sectional images, a three-dimensional image through which the inside of the sample can be seen is constructed.

In recent years, a device pattern has become minute due to density growth or reduction in size of a semiconductor device. Therefore, in the cross-section processing-and-observation, it is required that a more minute observation target can be observed with a higher resolution than in the past. In order to perform cross-section processing-and-observation of a sample including a minute observation target, it is necessary that a high-density cross-sectional image be acquired to enhance the resolution of the cross-sectional image.

However, when an attempt to enhance the resolution of a cross-sectional image is made in the cross-section processing-and-observation, there is a problem in that the time required to obtain a cross-sectional image increases and the time required to construct a three-dimensional image of one sample increases significantly. Therefore, a cross-section processing-and-observation method and a cross-section processing-and-observation apparatus which are capable of constructing a high-resolution three-dimensional image of a sample including a minute observation target within a short period of time are required.

An aspect of the present invention has been made in consideration of the above-described circumstances, and an object thereof is to provide a cross-section processing-and-observation method and a cross-section processing-and-observation apparatus which are capable of obtaining plural cross-sectional images of a minute observation target with a high resolution within a short period of time.

SUMMARY OF THE INVENTION

In order to solve the above-described problems, according to aspects of the present invention, a cross-section processing-and-observation method and a cross-section processing-and-observation apparatus which are described below are provided.

That is, according to an aspect of the present invention, there is provided a cross-section processing-and-observation method including: a cross-section exposure step of irradiating a focused a sample with ion beam to expose a cross-section of the sample; a cross-sectional image acquisition step of irradiating the cross-section with an electron beam to acquire a cross-sectional image of the cross-section; and a step of repeatedly performing the cross-section exposure step and the cross-sectional image acquisition step along a predetermined direction of the sample at a setting interval to acquire plural cross-sectional images of the sample, in which in the cross-sectional image acquisition step, a cross-sectional image is acquired under different condition settings for plural regions of the cross-section. As a result, for example, when a region including the entire portion of a cross-section and a region including only a part of the inside of the cross-section are observed as plural regions of the cross-section, cross-sectional images of the respective regions can be observed under different condition settings. In this way, only a desired region can be efficiently observed, and information of a cross-section can be acquired in more detail.

In the above-described cross-section processing-and-observation method, conditions of the cross-sectional image acquisition step may include at least one of an accelerating voltage of the electron beam, a current value of the electron beam, an aperture value of an object lens, an astigmatism correction amount, a brightness, a contrast, a magnification, an imaging time of the cross-sectional image, the number of times of acquiring a cross-sectional image for each cross-section, a pixel size, and a detector used for acquiring an cross-sectional image. The pixel described here refers to a unit pixel of a cross-sectional image.

In the above-described cross-section processing-and-observation method, the setting interval may be equal to or an integer multiple of a pixel size of any one of the plurality of regions, or the pixel size may be an integer multiple of the setting interval. As a result, when a three-dimensional image is constructed, a relationship between a pixel of a cross-section and a slice interval, that is, the size of a voxel which is a pixel of the three-dimensional image is clarified. Therefore, the three-dimensional image is visually easily recognized.

The above-described cross-section processing-and-observation method may further include a specific observation target detection step of detecting a predetermined specific observation target, in which in the specific observation target detection step, after a predetermined specific observation target is detected, a condition setting of the cross-section exposure step and a condition setting of the cross-sectional image acquisition step may be updated.

In the above-described cross-section processing-and-observation method, when the conditions of the cross-section exposure step are updated, the setting interval may be set to be shorter than that before the specific observation target is detected.

In the above-described cross-section processing-and-observation method, plural types of the specific observation targets may be set, and different condition settings of the cross-section exposure step and different condition settings of the cross-sectional image acquisition step may be set for individual regions where the respective specific observation targets are detected.

In the above-described cross-section processing-and-observation method, when the condition setting of the cross-section exposure step and the condition setting of the cross-sectional image acquisition step are set, the setting interval may be equal to or an integer multiple of a pixel size of the cross-sectional image.

In the above-described cross-section processing-and-observation method, in the specific observation target detection step, an EDS measurement or an EBSD measurement of the cross-section may be performed.

In the above-described cross-section processing-and-observation method, in the specific observation target detection step, a contrast change of a cross-sectional image obtained in the cross-sectional image acquisition step may be observed.

In the above-described cross-section processing-and-observation method, the conditions of the cross-section exposure step may include at least one of an accelerating voltage of the focused ion beam, a current value of the focused ion beam, an irradiation range of the focused ion beam in the sample, and a visual field range of the focused ion beam.

In the above-described cross-section processing-and-observation method, the specific observation target detection step may be performed once while the cross-sectional image acquisition step is performed multiple times.

In the above-described cross-section processing-and-observation method, in the specific observation target detection step performed after the specific observation target is detected, cross-section processing-and-observation may not be performed on other portions of the sample when the specific observation target is not detected anymore.

The above-described cross-section processing-and-observation method may further include a step of forming a correction mark by irradiation of the focused ion beam, in which in the cross-section exposure step, an image of the correction mark may be acquired with a higher magnification than the visual field range of the focused ion beam among the conditions of the cross-section exposure step.

The above-described cross-section processing-and-observation method may further include a step of forming a correction mark by irradiation of the focused ion beam, in which in the cross-sectional image acquisition step, when the cross-sectional image is acquired, an image of the correction mark may be acquired at the same time with a higher magnification than the magnification of a cross-section observation region observed by the electron beam among the conditions of the cross-sectional image acquisition step.

According to another aspect of the present invention, there is provided a cross-section processing-and-observation apparatus including: a sample stage on which a sample is placed; a focused ion beam column that irradiates the sample with a focused ion beam; an electron beam column that irradiates the sample with an electron beam; a secondary electron detector or backscattered electron detector that detects secondary electrons or backscattered electrons generated from the sample; and a control unit that repeatedly performs a cross-section exposure step, in which the sample is irradiated with a focused ion beam to expose a cross-section of the sample, and a cross-sectional image acquisition step, in which the cross-section is irradiated with an electron beam to acquire a cross-sectional image of the cross-section, along a predetermined direction of the sample at a setting interval to acquire a cross-sectional image under different conditions for plural regions of the cross-section in the cross-sectional image acquisition step.

In the above-described cross-section processing-and-observation apparatus, the control unit may control the setting interval to be equal to or an integer multiple of a pixel size of any one of the plurality of regions or may control the pixel size to be an integer multiple of the setting interval.

In the above-described cross-section processing-and-observation method, in a specific observation target detection step of detecting a predetermined specific observation target, after the predetermined specific observation target is detected, the control unit may update conditions of the cross-section exposure step and conditions of the cross-sectional image acquisition step.

According to the present invention, since only a desired minute region is observed with a high resolution, a cross-sectional image can be acquired within a short period of time. As a result, a high-resolution three-dimensional image including a desired observation target can be constructed within a short period of time.

DETAILED DESCRIPTION OF THE EMBODIMENTS

Figure 1:
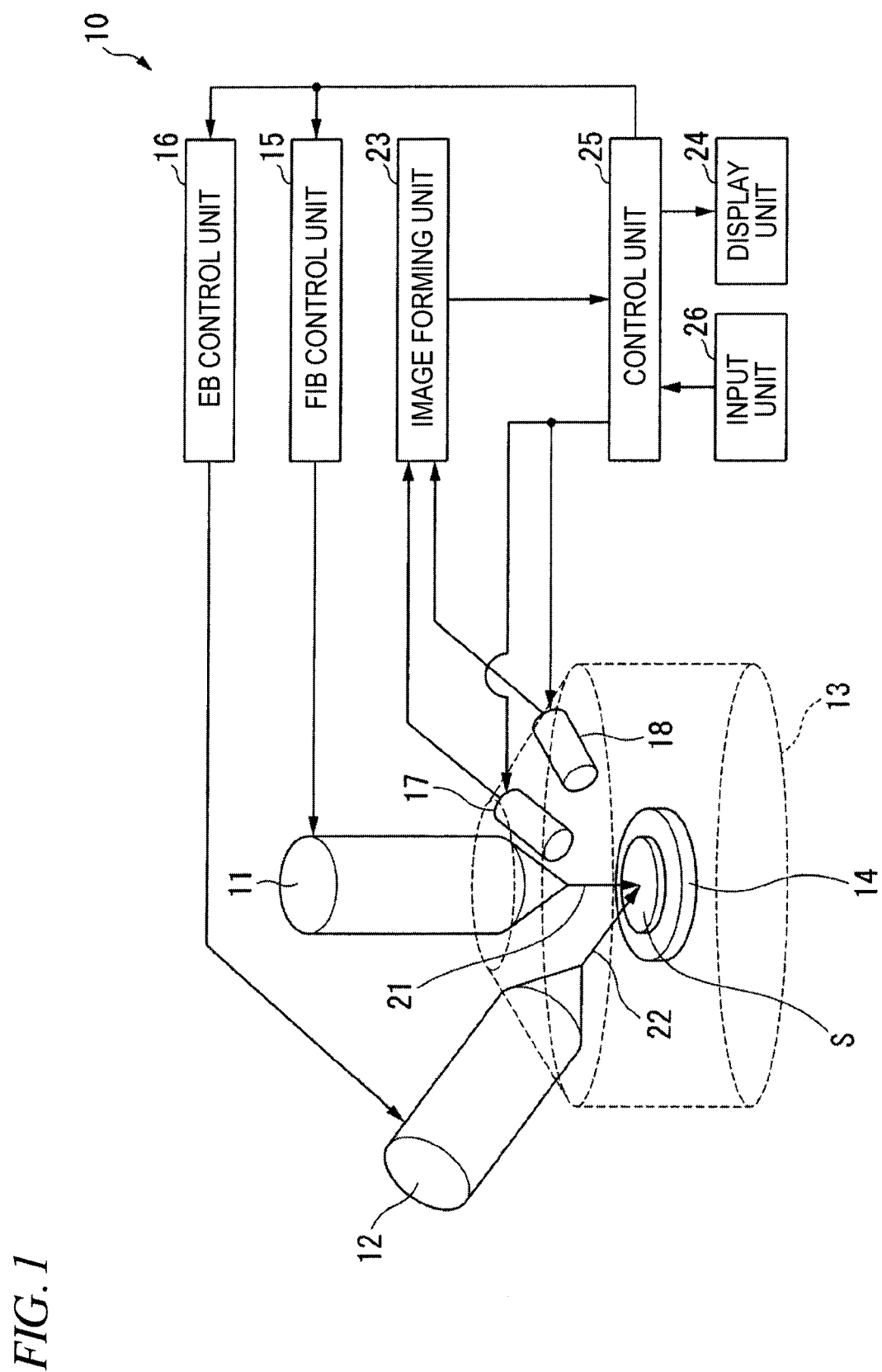
FIG. 1 is a schematic configuration diagram illustrating a cross-section processing-and-observation apparatus according to the present invention.

Hereinafter, a cross-section processing-and-observation method and a cross-section processing-and-observation apparatus according to the illustrative embodiment will be described. Respective illustrative embodiments described below are specific examples for easily understanding the scope of the present invention and do not limit the present invention unless specified otherwise. In addition, in the drawings used in the following description, major components may be enlarged and illustrated in order to make characteristics of the present invention easier to understand, and a dimensional ratio of each component may not be the same as that of the actual one.

(Cross-Section Processing-and-Observation Apparatus)

FIG. 1 is a schematic configuration diagram illustrating a cross-section processing-and-observation apparatus. A cross-section processing-and-observation apparatus 10 according to the illustrative embodiment includes a focused ion beam (FIB) column 11, an electron beam (EB) column 12, and a sample chamber 13. The focused ion beam column 11 and the electron beam column 12 are accommodated in the sample chamber 13 and are arranged therein so as to irradiate a sample S placed on a stage (sample stage) 14 with a focused ion beam (FIB) and an electron beam (EB). The stage 14 can move, tilt and rotate in any of X, Y, and Z directions so as to be able to adjust the sample S in an arbitrary direction.

It is preferable that the focused ion beam (FIB) column 11 and the electron beam (EB) column 12 be arranged such that beams emitted from the respective columns are respectively perpendicular to the sample S. This is because an electron beam can be emitted in a direction perpendicular to a processed cross-section, and a high-resolution cross-sectional image can be acquired.

The cross-section processing-and-observation apparatus 10 further includes a focused ion beam (FIB) control unit 15 and an electron beam (EB) control unit 16. The focused ion beam control unit 15 controls the focused ion beam column 11 and emits a focused ion beam at an arbitrary time. The electron beam control unit 16 controls the electron beam column 12 and emits an electron beam at an arbitrary time.

The cross-section processing-and-observation apparatus 10 further includes a secondary electron detector 17 and an EDS detector 18. The secondary electron detector 17 irradiates the sample S with a focused ion beam 21 or an electron beam 22 and detects secondary electrons generated from the sample S. In addition, the EDS detector 18 irradiates the sample S with the electron beam 22 and detects an X-ray generated from the sample S. The X-ray generated from the sample S includes a characteristic X-ray unique to a material included in the sample S. The material included in the sample S can be specified based on the characteristic X-ray.

Instead of the secondary electron detector 17, a backscattered electron detector is also preferably provided. The backscattered electron detector detects backscattered electrons obtained by the electron beam being backscattered from the sample S. A cross-sectional image can be acquired from these backscattered ions.

In addition, instead of the EDS detector 18, an EBSD detector is also preferably provided. In the EBSD detector, when a crystalline material is irradiated with an electron beam, a diffraction pattern, that is, an EBSD pattern is observed by electron backscatter diffraction occurring on the surface of the sample S, and information pertaining to the crystal system or crystal orientation of the sample S is obtained. By measuring and analyzing such an EBSD pattern, information pertaining to the distribution of the crystal system or crystal orientation of a minute region of the sample S can be obtained, and a material included in the sample S can be specified.

Further, instead of using the EDS detector 18, a configuration may be adopted in which a specific observation target is detected by comparing the contrast of an observation image, which is obtained in an image forming unit 23 described below, to the contrast of, for example, a reference image which is stored in advance.

The cross-section processing-and-observation apparatus 10 further includes an image forming unit 23 that forms an observation image of a cross-section of the sample S and a display unit 24 that displays the observation image. The image forming unit 23 forms a SIM image based on a signal for scanning the focused ion beam 21 and a signal of the secondary electrons detected by the secondary electron detector 17. The display unit 24 displays the SIM image obtained by the image forming unit 23. The display unit 24 may be configured of, for example, a display apparatus.

In addition, the image forming unit 23 forms a SEM image based on a signal for scanning the electron beam 22 and the signal of the secondary electrons detected by the secondary electron detector 17. The display unit 24 displays the SEM image obtained by the image forming unit 23. In addition, the image forming unit 23 forms an EDS map based on the signal for scanning the electron beam 22 and a signal of the characteristics X-ray detected by the EDS detector 18. The display unit 24 displays the EDS map obtained by the image forming unit 23. The EDS map specifies a material of the sample S at each electron beam irradiation point from energy of the detected characteristic X-ray, and shows distribution of material in an irradiation region of the electron beam 22.

The cross-section processing-and-observation apparatus 10 further includes a control unit 25 and an input unit 26. An operator inputs various control conditions of the cross-section processing-and-observation apparatus 10 through the input unit 26. The input unit 26 transmits the input information to the control unit 25. The control unit 25 outputs control signals to the focused ion beam control unit 15, the electron beam control unit 16, and the image forming unit 23, and controls the overall operation of the cross-section processing-and-observation apparatus 10.

In the cross-section processing-and-observation apparatus 10, it is preferable that a source gas supply mechanism be further formed to form a deposition film for protecting the surface of the sample S. The deposition film for protecting the surface of the sample S is formed through the source gas supply mechanism. On the deposition film, a correction mark which is a positioning index for combining plural cross-sectional images can be formed, for example, in a step of forming a three-dimensional image of the sample S described below. The correction mark is the linear index that extends along a direction (hereinafter, referred to as "predetermined direction") in which the deposition film is irradiated with the focused ion beam 21 to sequentially slice the sample S.

Figure 2:
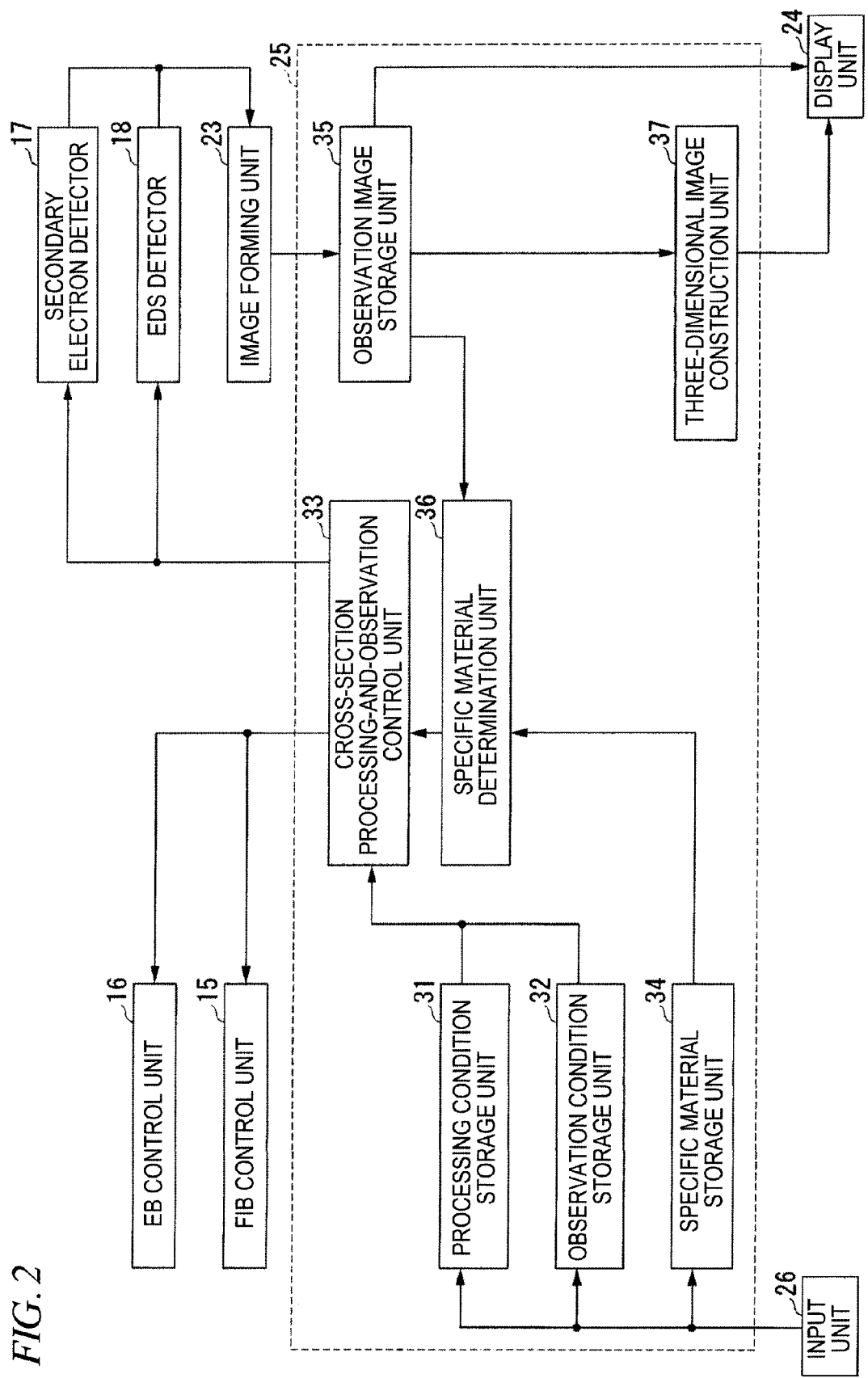
FIG. 2 is a schematic configuration diagram illustrating a configuration of a control unit of the cross-section processing-and-observation apparatus.

FIG. 2 is a schematic configuration diagram illustrating a configuration of a control unit of the cross-section processing-and-observation apparatus.

The control unit 25 includes a processing condition storage unit 31, an observation condition storage unit 32, a cross-section processing-and-observation control unit 33, a specific material storage unit 34, an observation image storage unit 35, a specific material determination unit 36, and a three-dimensional image construction unit 37.

The processing condition storage unit 31 stores a setting value of a slicing interval of the sample S and setting values of the position and size of a processing region of the focused ion beam 21 in the sample S. The processing condition storage unit 31 stores: a slicing interval (hereinafter, referred to as "high-speed processing interval") which is set when one or plural types of preset specific observation targets are not detected in the sample S; and a slicing interval (hereinafter, referred to as "precise processing interval") which is narrower than the high-speed processing interval and is set when the specific observation targets are detected in the sample S. It is preferable that plural setting values corresponding to the sizes and types of the specific observation targets be stored as the precise processing interval.

In addition, the processing condition storage unit 31 stores: a setting value of the size of a processing region of the sample S which is set when the processing region is sliced at the high-speed processing interval; and a setting value of the size of a processing region of the sample S which is set when the processing region is sliced at the precise processing interval.

In addition, the processing condition storage unit 31 stores setting values of an accelerating voltage and a current of the focused ion beam 21. When the focused ion beam 21 which is accelerated at a low accelerating voltage is used, a damage layer formed on the sample S can be reduced. In addition, when the focused ion beam 21 having a low current is used, the width of a beam shape is narrow. Therefore, a steep cross-section can be formed, which is preferable, particularly, when a minute observation target is processed. Accordingly, the processing condition storage unit 31 stores a setting value of a high current for slicing at the high-speed processing interval and a setting value of a low current for slicing at the precise processing interval. It is preferable that setting values of a low current having the number corresponding to the types of the precise processing interval be set.

The observation condition storage unit 32 stores setting values of the position and size of an observation region of the sample S and setting values of an accelerating voltage and a current of the electron beam 22. When the electron beam 22 which is accelerated at a low accelerating voltage is used, the penetration length of the electron beam 22 through the sample S is short. Therefore, an observation image on which only information of the vicinity of a cross-section is reflected can be acquired. In addition, when the electron beam 22 having a low current is used, the width of a beam shape is narrow, and thus a high-resolution observation image can be acquired. Therefore, it is preferable that the electron beam 22 having a low current be used when a minute observation target is observed.

On the other hand, when the accelerating voltage of the electron beam 22 is high, the penetration length of the electron beam 22 through the sample S increases. Therefore, an observation image on which information of the inside of the sample S is reflected can be acquired, and a minute observation target is easily detected. Accordingly, the observation condition storage unit 32 stores: setting values of a high accelerating voltage and a high current which are set to perform cross-section observation for detecting a large observation target and a minute observation target; and setting values of a low accelerating voltage and a low current which are set to observe a minute observation target. It is preferable that plural setting values corresponding to the sizes and types of the preset specific observation targets be set as the setting values of a low accelerating voltage and a low current which are set to observe a minute observation.

The observation condition storage unit 32 further stores an aperture value of an object lens of the electron beam column 12, an astigmatism correction amount, a brightness, a contrast, a magnification, an imaging time of an observation image (cross-sectional image) of the sample S, the number of times of acquiring an observation image, a pixel size, and the like.

In addition, the observation condition storage unit 32 stores various types of observation images. The types of observation images include a SEM image, a backscattered electron image, a SIM image, and an EDS image. When the SEM image and the SIM image are acquired, the secondary electrons are detected by the secondary electron detector 17, and the SEM image and the SIM image are formed by the image forming unit 23. When the EDS image is acquired, the characteristic X-ray is detected by the EDS detector 18, and the EDS map is formed by the image forming unit 23. In addition, when the backscattered electron image is acquired, the backscattered electrons are detected by the backscattered electron detector inside the electron beam column 12, and the backscattered electron image is formed by the image forming unit 23.

The specific material storage unit 34 stores an element of the material included in the specific observation target. When the element is detected by the EDS measurement in the cross-section processing-and-observation for detecting a minute observation target, conditions of the cross-section processing-and-observation, that is, conditions of a cross-section exposure step and conditions of a cross-sectional image acquisition step are updated. The cross-section exposure step and the cross-sectional image acquisition step will be described below.

When an operator inputs the above-described respective setting values and the element of the material included in the specific observation target through the input unit 26, the respective storage units of the cross-section processing-and-observation apparatus 10 stores the setting values and the element. The stored setting values of the processing conditions and the observation conditions are read by the cross-section processing-and-observation control unit 33. In addition, the element of the specific observation target is output from the specific material determination unit 36.

The cross-section processing-and-observation control unit 33 outputs irradiation conditions of the focused ion beam 21, that is, processing conditions of the sample S to the focused ion beam column 11. As a result, the focused ion beam column 11 irradiates the sample S with the focused ion beam 21 to etch the sample in a predetermined shape such that a cross-section at an arbitrary position is exposed.

The cross-section processing-and-observation control unit 33 outputs irradiation conditions of the electron beam 22, that is, processing conditions of the sample S to electron beam column 12. The electron beam column 12 irradiates the sample S with the electron beam 22 and acquires, for example, an observation image of the sample S from secondary electrons or an X-ray generated from a cross-section of the sample S which is formed by the focused ion beam 21.

According to the type of an observation image to be acquired, the cross-section processing-and-observation control unit 33 controls the secondary electron detector 17, the backscattered electron detector, or the EDS detector 18 to detect the secondary electrons, the backscattered electrons, or the characteristic X-ray generated from the sample S. Based on the detected secondary electrons, backscattered electrons, or characteristic X-ray, an observation image is formed by the image forming unit 23.

The observation image storage unit 35 stores the observation image formed by the image forming unit 23. The display unit 24 displays the observation image stored in the observation image storage unit 35. Further, when a three-dimensional image described below is constructed from the obtained plural observation images, the three-dimensional image construction unit 37 sequentially reads the plural observation images stored in the observation image storage unit 35 to construct the three-dimensional image. This three-dimensional image is displayed by the display unit 24.

The specific material determination unit 36 reads the element of the material, which is included in the previously stored specific observation target, from the specific material storage unit 34 during the execution of the cross-section processing-and-observation and reads the EDS map, which is acquired in the cross-section processing-and-observation, from the observation image storage unit 35. When the element appears on the EDS map, that is, when the specific observation target is detected, the specific material determination unit 36 transmits a signal to the cross-section processing-and-observation control unit 33. After the cross-section processing-and-observation control unit 33 receives the signal, a condition setting of the cross-section exposure step and a condition setting of the cross-sectional image acquisition step are updated.

(Summary of Cross-Section Processing-and-Observation Method)

Figure 3A:
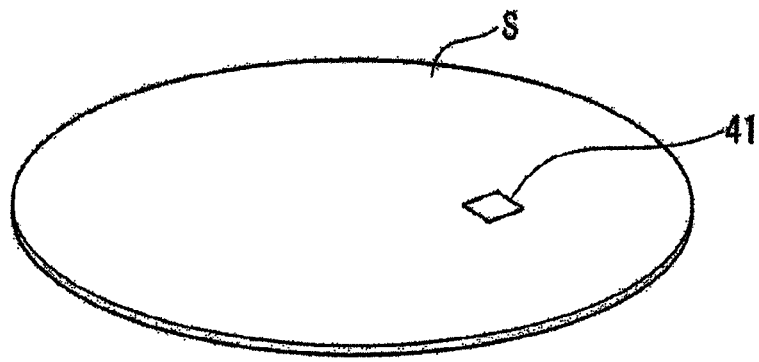
FIGS. 3A to 3C are diagrams illustrating a state where cross-section processing-and-observation of a semiconductor wafer is performed.
Figure 3B:
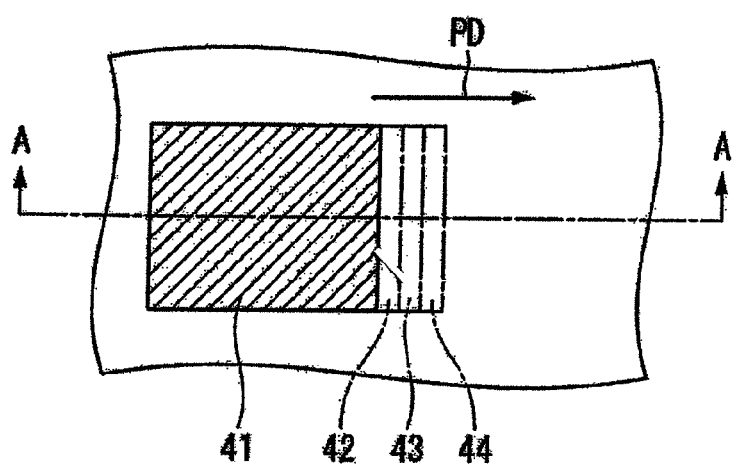
Figure 3C:
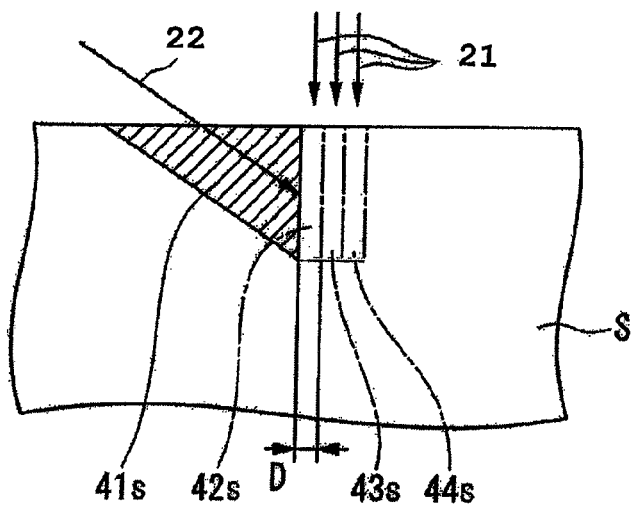

The summary of a cross-section processing-and-observation method in which the cross-section processing-and-observation apparatus having the above-described configurations is used will be described. Here, for example, a case where a semiconductor wafer is used as a sample of an observation target will be described as an example. FIGS. 3A to 3C are diagrams illustrating a state where cross-section processing-and-observation of a semiconductor wafer is performed. FIG. 3A illustrates a processing groove of the semiconductor wafer. FIG. 3B is an enlarged view illustrating the periphery of the processing groove. FIG. 3C is a cross-sectional view taken along line A-A of FIG. 3B. The sample (semiconductor wafer) S has a minute device structure therein. In the cross-section processing-and-observation, cross-sectional observation images of desired observation targets such as a device structure and defects inside the sample S are acquired and analyzed. When the observation target is minute, it is difficult to accurately detect a position thereof in the sample S due to the positioning accuracy of the stage and the accuracy of device processing.

Accordingly, the focused ion beam 21 is emitted in the vicinity of a position where the observation target is assumed to be present to form a processing groove 41 by etching. A processing region of the cross-section processing is set such that the processing groove 41 is widened to the position where the observation target is assumed to be present. In the following description, a direction in which the processing groove 41 is widened to the position where the observation target is assumed to be present will be referred to as "predetermined direction (processing progression direction) PD".

As the processing groove 41 to be formed on the sample (semiconductor wafer) S, a slope shape whose depth from the surface of the sample S gradually increases toward the predetermined direction PD is formed in advance such that the electron beam 22 can be emitted onto a formed cross-section (observation surface) 41s. The processing groove 41 is widened along the predetermined direction PD in order of processing regions 42, 43, 44, . . . of slicing from the cross-section 41s. Whenever the processing of each of the processing regions 42, 43, 44, . . . is completed, the electron beam 22 is emitted onto a rectangular cross-section (observation surface), which is exposed by the processing along the thickness direction of the sample S, to acquire an observation image. In addition, the EDS map is also acquired from all the cross-sections or after several times or several tens of times of processing.

A slicing interval (setting interval) D of slicing of each of the processing regions 42, 43, 44, . . . is updated before and after the preset specific observation target is detected. For example, when the specific observation target is detected, the slicing interval D is updated to be narrower than that before the detection. This update of the slicing interval D is performed by updating the conditions of the cross-section exposure step.

In addition, conditions of acquiring an observation image of each cross-section after the completion of slicing of each of the processing regions 42, 43, 44, . . . are updated before and after the preset specific observation target is detected. This update of the conditions of acquiring an observation image of each cross-section is performed by updating the condition setting of the cross-sectional image acquisition step. The conditions of the cross-section exposure step and the conditions of the cross-sectional image acquisition step will be described below.

As described above, the processing region 42 is etched by the focused ion beam 21, the exposed cross-section 42s is irradiated with the electron beam 22, and the observation image and the EDS map of the cross-section 42s are acquired. Next, the processing region 43 is etched by the focused ion beam 21, and the observation image of the exposed cross-section 43s is acquired. Next, the processing region 44 is etched by the focused ion beam 21, the exposed cross-section 44s is irradiated with the electron beam 22, and the observation image of the cross-section 44s is acquired. By repeatedly performing the cross-section processing and the cross-section observation (Cut&See), the plural observation images of the cross-sections along the predetermined direction PD are acquired. By performing image processing of sequentially combining these plural observation images, a three-dimensional image of a predetermined region of the sample S can be acquired.

(First Embodiment of Cross-Section Processing-and-Observation Method)

Next, a method in which, based on the summary of the above-described cross-section processing-and-observation method, cross-section processing-and-observation is performed while updating a condition setting of the cross-section exposure step and a condition setting of the cross-sectional image acquisition step to construct a three-dimensional image of an observation target will be described with reference to FIGS. 1, 2, and 4 to 9B. In the following embodiment, a case of setting two types of specific observation targets and performing cross-section processing-and-observation of a sample in which the two types of specific observation targets are present close to each other is assumed.

Figure 4:
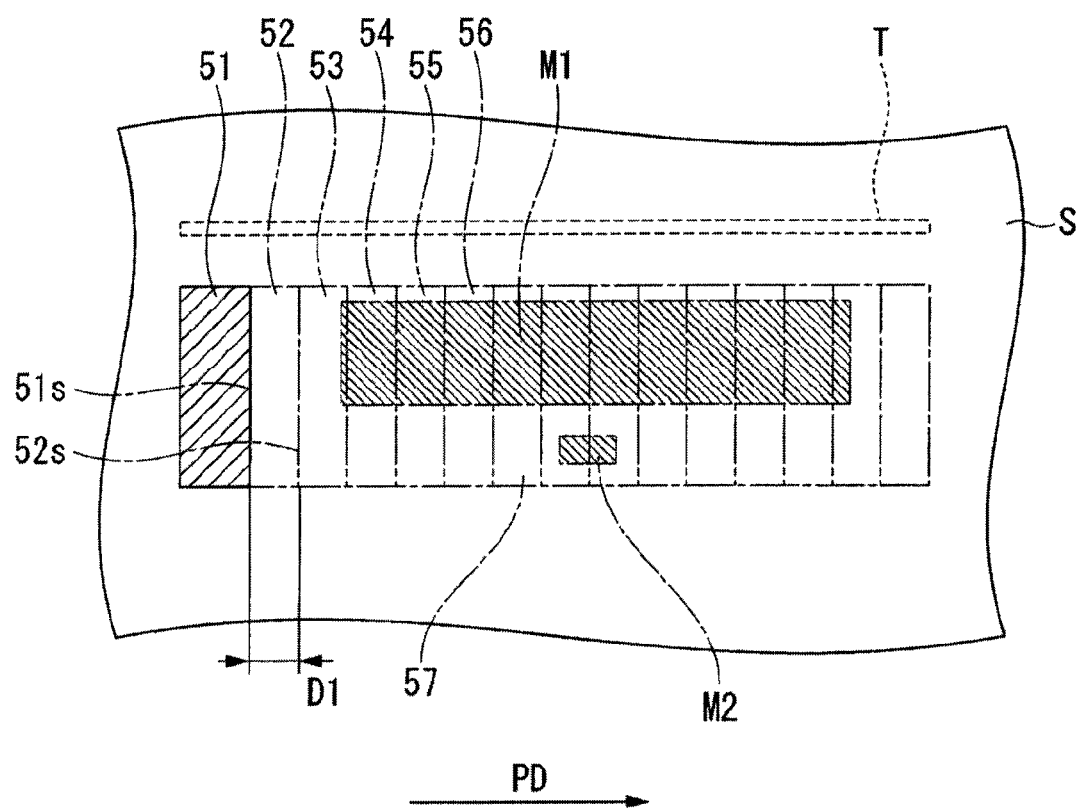
FIG. 4 is a diagram illustrating a cross-section processing-and-observation method according to a first embodiment of the present invention.

FIG. 4 illustrates a sample S including a specific material M1 and a specific material M2 which are specific observation targets. A deposition film (not illustrated) is formed on the sample S in advance, and a correction pattern T is formed on the deposition film to linearly extend along the predetermined direction (processing progression direction) PD. This correction pattern T is formed by, for example, irradiation of the focused ion beam 21.

First, in the vicinity of a position where the specific material M1 and the specific material M2 are assumed to be present, a slope-shaped processing groove 51 is formed by etching using the focused ion beam 21. Next, a condition setting for cross-section processing-and-observation is set. In the condition setting of the cross-section exposure step, in order to detect the specific materials M1 and M2, the position and size of a processing region 52 are set at a slicing interval of D1 of, for example, 50 nm. In addition, as the condition setting of the cross-sectional image acquisition step, the accelerating voltage of the electron beam 22 is set as, for example, 5 kV. In addition, carbon and iron are set as constitutional elements of the specific materials. In the embodiment, it is assumed that the specific material M1 is carbon and the specific material M2 is iron.

When a cross-section is observed with the electron beam 22 which is accelerated at an accelerating voltage of 5 kV, the penetration length of the electron beam 22 through the sample S is about 50 nm. Therefore, when the cross-section is irradiated with the electron beam 21 at the slicing interval D1 of 50 nm, the electron beam 22 is incident within the next slicing range, that is, within a range of the slicing interval D1. Thus, when being present in this range, the specific material M1 and the specific material M2 can be detected. As a result, even if the sizes of the specific material M1 and the specific material M2 are the slicing interval D1 or less, the specific material M1 and the specific material M2 can be detected with the cross-section processing-and-observation at the slicing interval D1.

Next, a cross-section 52s which is formed by slicing is irradiated with the electron beam 22 to acquire a SEM observation image of the cross-section 52s. In addition, an X-ray generated by irradiation of the electron beam 22 is detected by the EDS detector 18. At this time, a characteristic X-ray of silicon, oxygen, aluminum, copper, or the like which is a material included in a device is detected from the sample S which is a semiconductor wafer. The image forming unit 23 forms an EDS map, which is a material distribution in an irradiation region of the electron beam 21, based on the irradiation position of the electron beam 21 and the detected characteristic X-ray. Slicing and EDS map forming are repeatedly performed. When carbon as the specific material M1 or iron as the specific material M2 appears on the EDS map, conditions of the cross-section exposure step and conditions of the cross-sectional image acquisition step are updated.

For example, when a processing region 53 is sliced, carbon as the specific material M1 is detected at a cross-section 53s of the processing region 53. Here, conditions of the cross-sectional image acquisition step are updated. For example, in order to observe the specific material M1 in more detail to acquire a detailed three-dimensional image, a minute region including the specific material M1 is set in the cross-section s. A condition setting is set such that only the minute region including the specific material M1 can be observed with a higher magnification than an observation magnification of the entire cross-section s. As a result, the observation image of the entire cross-section s and the high-magnification observation image only for the minute region including the specific material M1 are acquired.

The condition setting of the cross-sectional image acquisition step includes, for example, an accelerating voltage of the electron beam 21, a current value of the electron beam 21, an aperture value of an object lens of the electron beam column 12, an astigmatism correction amount, a brightness of an observation image, a contrast, a magnification, an imaging time of the observation image, the number of times of acquiring an observation image for each cross-section, a pixel size, and a detector used for acquiring an cross-sectional image. By updating these conditions of the cross-sectional image acquisition step in the cross-section where the preset specific material is detected, the observation image of the entire cross-section s and the high-magnification and high-resolution observation image only for the minute region including the specific material are acquired.

Next, in a state where the conditions of the cross-sectional image acquisition step are updated, the slicing of processing regions 54 to 56 and the acquisition of an observation image of a cross-section in each processing region are performed along the predetermined direction PD. During this time, while the specific material M1 is detected, the observation image of the entire cross-section s and the high-resolution observation image only for the minute region including the specific material M1, which is observed with a higher magnification than an observation magnification of the entire cross-section s, are acquired.

When slicing is further performed along the predetermined direction PD, iron as the specific material M2 is detected in, for example, a cross-section 57s of a processing region 57. Here, conditions of the cross-sectional image acquisition step are updated, and conditions of the subsequent cross-section exposure step are updated.

For example, in order to observe the specific material M2 in more detail to acquire a detailed three-dimensional image, a minute region including the specific material M2 is set in the cross-section s. A condition setting is set such that only the minute region including the specific material M2 can be observed with a higher magnification than an observation magnification of the entire cross-section s. As a result, the observation image of the entire cross-section s, the high-magnification observation image only for the minute region including the specific material M1, and the high-magnification observation image only for the minute region including the specific material M2 are acquired.

The condition setting of the cross-sectional image acquisition step includes, for example, an accelerating voltage of the electron beam 21, a current value of the electron beam 21, an aperture value of an object lens of the electron beam column 12, an astigmatism correction amount, a brightness of an observation image, a contrast, a magnification, an imaging time of the observation image, the number of times of acquiring a observation image for each cross-section, and a pixel size. By updating these conditions of the cross-sectional image acquisition step in the cross-section where the preset specific material is detected, the observation image of the entire cross-section s and the high-magnification and high-resolution observation images only for the minute regions including the respective specific material are acquired.

Figure 5:
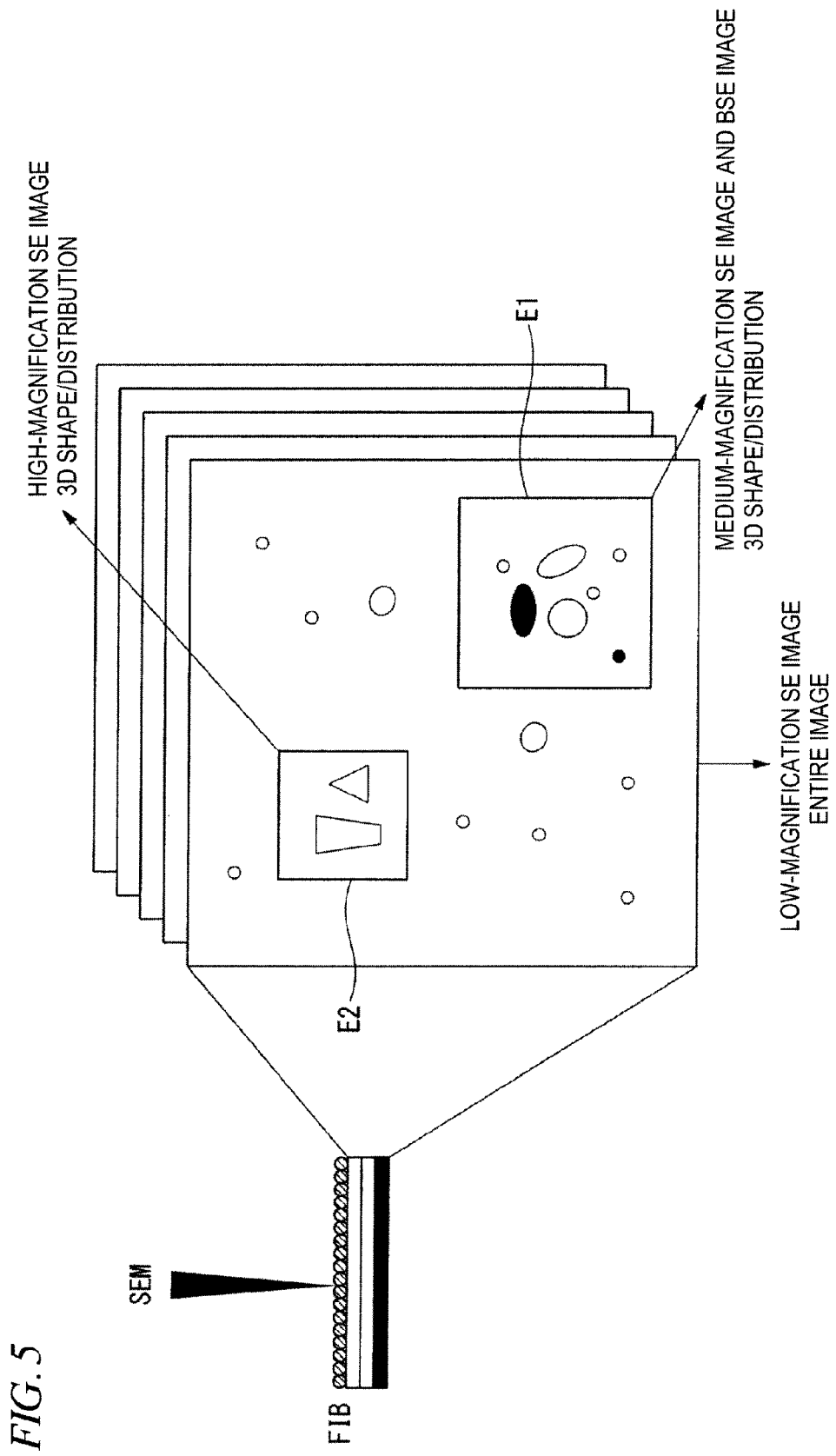
FIG. 5 is a schematic diagram illustrating observation images of cross-sections.

FIG. 5 is a schematic diagram of observation images of a cross-section. In an example of the observation images of the cross-section illustrated in FIG. 5, observation images are acquired from two minute regions E1 and E2 including specific observation targets under different acquisition conditions from those of an observation image of the entire cross-section. For example, when the observation image of the entire cross-section is acquired with a low magnification, an SEM image is acquired from the minute region E1 with a medium magnification. In addition, by acquiring a BSE image, a composition distribution in the minute region E1 is obtained. On the other hand, when the observation image of the entire cross-section is acquired with a low magnification, an SEM image is acquired from the minute region E2 with a high magnification.

In this way, plural minute regions including respective plural specific materials are set in a cross-section exposed by slicing, different condition settings of the cross-sectional image acquisition step are set for the individual minute regions. As a result, a highly accurate observation image having a shape and a composition of each of preset arbitrary specific materials can be acquired. In addition, an observation image is acquired from the entire cross-section exposed by slicing with, for example, a low magnification, and an observation image is selectively acquired from only a minute region including each of plural specific materials with a high magnification. As a result, as compared to a case where an observation image is acquired from the entire cross-section with a high resolution, the highly accurate shape and composition of a specific material can be effectively obtained within a short period of time.

When the condition setting of the cross-sectional image acquisition step is set, it is preferable that the type of an observation image of a cross-section be reflected on the setting value of the slicing interval in the condition setting of the cross-section exposure step. That is, for example, when a SEM image is used as an observation image, the setting value of the slicing interval is set to be an integer multiple of a resolution setting value of the SEM image. As a result, an error between the slicing interval of the sample S and the resolution of the SEM image can be eliminated. That is, in the case of a three-dimensional image, the size of a voxel which is a pixel of the three-dimensional image can be clarified, and three-dimensional information can be more accurately displayed.

Regarding the setting of a minute region in one cross-section, two minute regions are set in the above-described example. However, by setting three or more minute regions, different condition settings of the cross-sectional image acquisition step can be set for the individual minute regions.

Figure 6:
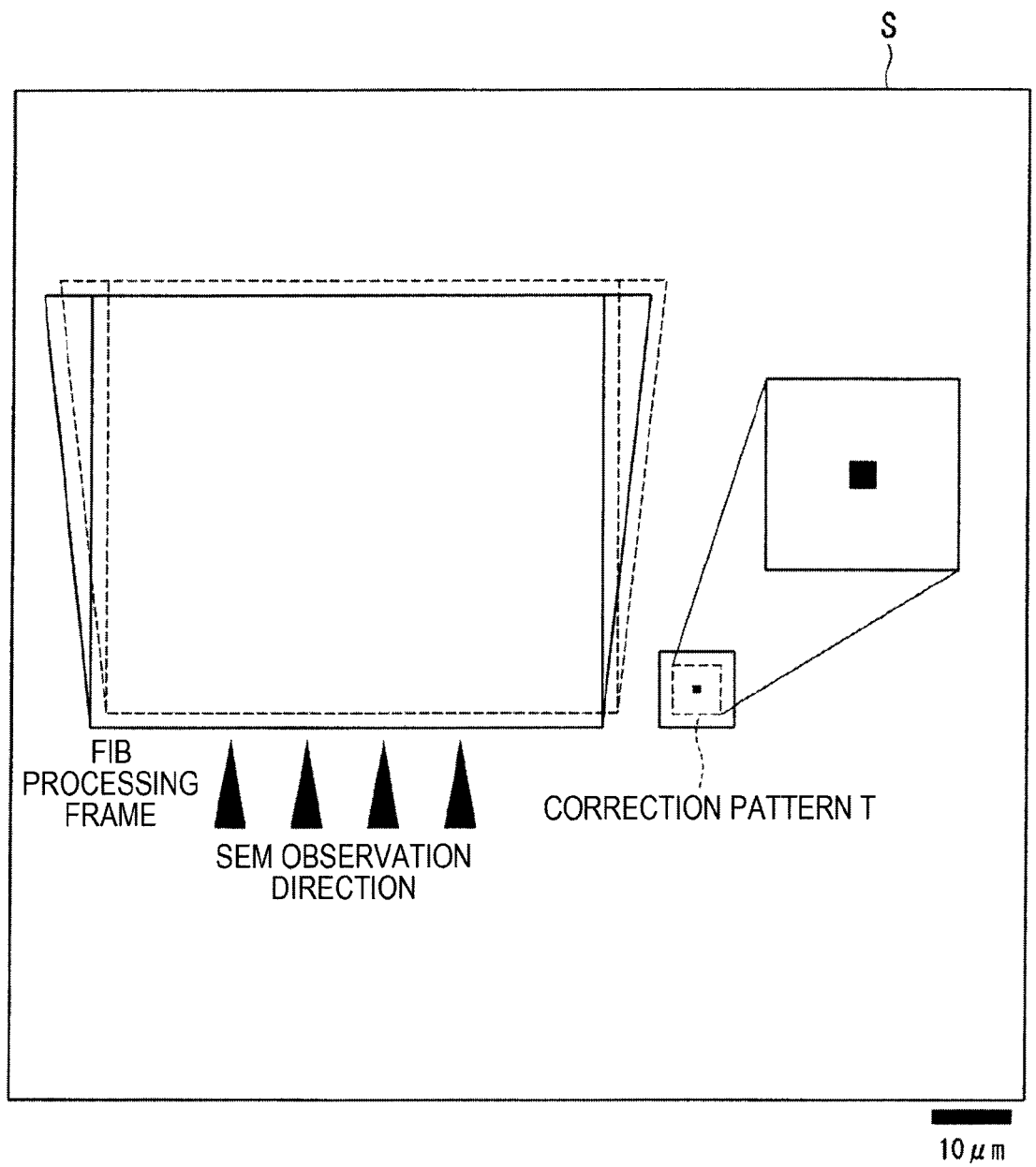
FIG. 6 is a diagram illustrating an observation image of a correction pattern.

When a continuous cross-section is processed by FIB, an image of the correction pattern T which is formed on the deposition film in advance is acquired. For example, as illustrated in FIG. 6, when a cross-section of the sample S is formed by the focused ion beam 21, the FIB is also emitted onto the correction pattern T which is formed in the vicinity of the cross-section to acquire an image of the correction pattern T at the same time. At this time, conditions of the cross-section exposure step of the correction pattern T are updated such that the image of the correction pattern T is acquired with a higher magnification than that of the SIM image acquired when the cross-section of the sample S is processed.

For example, the condition setting is performed such that the magnification of the observation image of the correction pattern T is four times that of the SIM image acquired when the cross-section of the sample S is processed. As a result, the accuracy of the correction pattern recognition can be made 4 times higher, and the accuracy of processing can be improved. In this way, when the image of the correction pattern T is acquired, the magnification is set to be higher than that of the SIM image acquired when the cross-section of the sample S is processed. As a result, each cross-section can be formed by FIB based on the correction pattern T with a higher accuracy than that of drift correction.

In addition, in a case where a three-dimensional image is constructed in the subsequent step, when an observation image is acquired from a cross-section which is formed for each of processing regions, an image of a correction pattern of electron beam which is formed outside an observation region of the cross-section is acquired. For example, when an observation image of a cross-section of the sample S which is formed by the focused ion beam 21 is acquired by irradiation of the electron beam 22, the correction pattern of electron beam which is formed in the vicinity of the observation region is also irradiated with the electron beam 22 to acquire an image of the correction pattern at the same time. At this time, conditions of the cross-sectional image acquisition step of the correction pattern are updated such that the image of the correction pattern is acquired with a higher magnification than that of the observation image of the cross-section of the sample S.

For example, the condition setting is performed such that the magnification of the observation image of the correction pattern T is four times that of the observation image of the cross-section of the sample S. As a specific example, if the visual field range of an observation image of a cross-section of the sample S is 10 μM and the pixel size thereof is 10 nm, when the magnification of an observation image of a correction pattern is four times that of the observation image of the cross-section of the sample S, the visual field range is 25 μm and the pixel size is 2.5 nm.

In this way, when the image of the correction pattern T is acquired, the magnification is set to be higher than that of the observation image of the cross-section of the sample S. As a result, when cross-sectional images of cross-sections can be combined based on the correction pattern in the subsequent step, correction of the combining of the cross-sectional images can be performed. In particular, when a high-magnification observation image is acquired from only a minute region including a specific material under acquisition conditions different from those of an observation image of the entire cross-section, a three-dimensional image which includes the high resolution image of the minute region including the specific material can be constructed by acquiring an observation image of a correction pattern with a high magnification according to the high magnification of the minute region.

Figure 7:
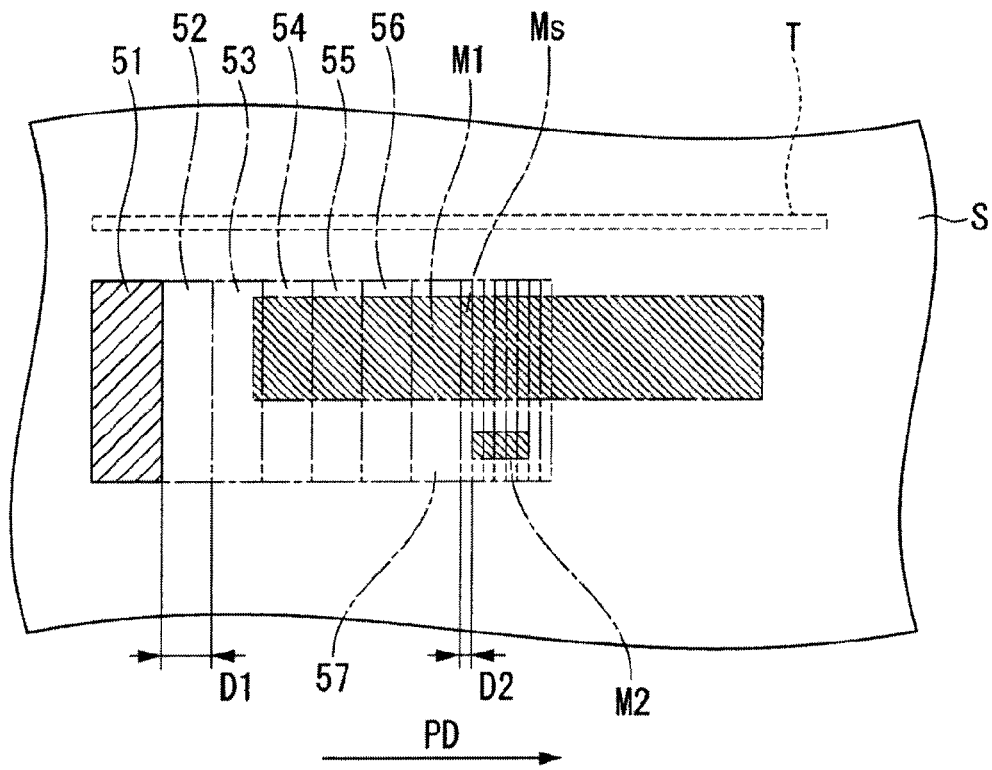
FIG. 7 is a diagram illustrating the cross-section processing-and-observation method according to the first embodiment

After iron as the specific material M2 is detected in the EDS map, conditions of the cross-section exposure step are updated. As illustrated in FIG. 7, in processing regions subsequent to the processing region 57 where the specific material M2 is detected, slicing is performed at a slicing interval D2 which is narrower than the slicing interval D1 of the processing regions 52 to 57 of the sample S. The slicing interval D2 is set as, for example, 5 nm.

The slicing interval is set to be an integer multiple of for example, a resolution setting value of the SEM image in the condition setting of the cross-sectional image acquisition step. As a result, an error between the slicing interval of the sample S and the resolution of the SEM image can be eliminated.

The conditions of the cross-section exposure step are updated by updating at least one of an accelerating voltage of the focused ion beam 21, a current value of the focused ion beam 21, an irradiation range of the focused ion beam 21 in the sample, and a visual field range of the focused ion beam 21.

After the conditions of the cross-section exposure step is updated and the specific material M2 is detected, other cross-sections are sliced at the slicing interval D2 which is narrower than the slicing interval D1 by about 5 nm. Even if the size of the specific material M2 is, for example, about 60 nm, 10 or more cross-sections Ms are formed from a minute region including the specific material M2, and observation images of the cross-sections Ms can be obtained. The minute region including the specific material M2 is set such that an observation image thereof is acquired with a higher magnification than an observation image of the entire cross-section by updating the conditions of the cross-sectional image acquisition step. Therefore, a three-dimensional image having a high-resolution image of the specific material M2 can be constructed by updating the conditions of the cross-section exposure step and the conditions of the cross-sectional image acquisition step and acquiring an observation image of the above-described correction pattern T with a higher magnification than that of the observation image of the entire cross-section.

In the above-described embodiment, after the specific material M2 is detected, other cross-sections are sliced in the same slicing range while reducing the slicing interval. However, for example, a configuration can also be adopted in which: in the case of the specific material M1, only the presence thereof needs to be confirmed; and in the case of the specific material M2, when it is desired to acquire a three-dimensional image of the entire shape thereof, only a minute region including the specific material M2 is sliced.

Figure 8:
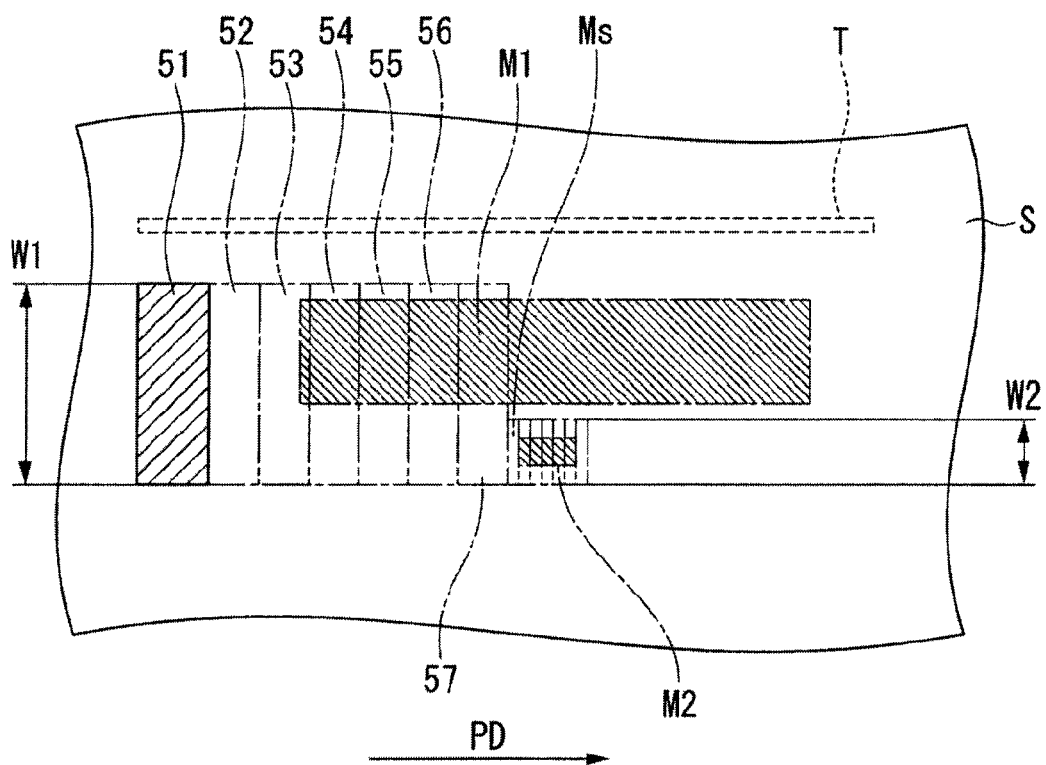
FIG. 8 is a diagram illustrating the cross-section processing-and-observation method according to the first embodiment.

In the embodiment illustrated in FIG. 8, in processing regions subsequent to the processing region 57 where the specific material M2 is detected, the conditions of the cross-section exposure step are updated, in which the irradiation region of the focused ion beam 21 in the sample S is limited to the minute region including the specific material M2 and slicing is performed at the slicing interval D2 which is narrower than the slicing interval D1.

In this way, by limiting the processing region of the sample S to the minute region including the specific material M2, a processing width W1 of the processing regions 52 to 57 is larger than a processing width W2 of processing regions subsequent to the processing regions 52 to 57. Therefore, the processing area is narrowed and the time required for processing is reduced. In addition, the acquisition range of an observation image in each cross-section is narrowed and the time required for acquiring a cross-sectional image is reduced. As a result, cross-section processing-and-observation can be efficiently performed within a short period of time.

A configuration can also be adopted in which the irradiation range of the focused ion beam 21 is limited to both a minute region including the specific material M1 and a minute region including the specific material M2, the plural minute regions are sliced, and an observation image is acquired from each of cross-sections thereof.

When the specific observation target (specific material) is detected, the condition setting of the cross-section exposure step and the condition setting of the cross-sectional image acquisition step are updated, and the cross-section processing-and-observation is performed. The cross-section processing-and-observation may be performed until the cross-section processing-and-observation of the entire preset range is completed. However, for example, the condition setting of the cross-section exposure step may be set such that the cross-section processing-and-observation ends at a position where the specific material M1 is not detected anymore or at a position where the specific material M2 is not detected anymore.

Figure 9A:
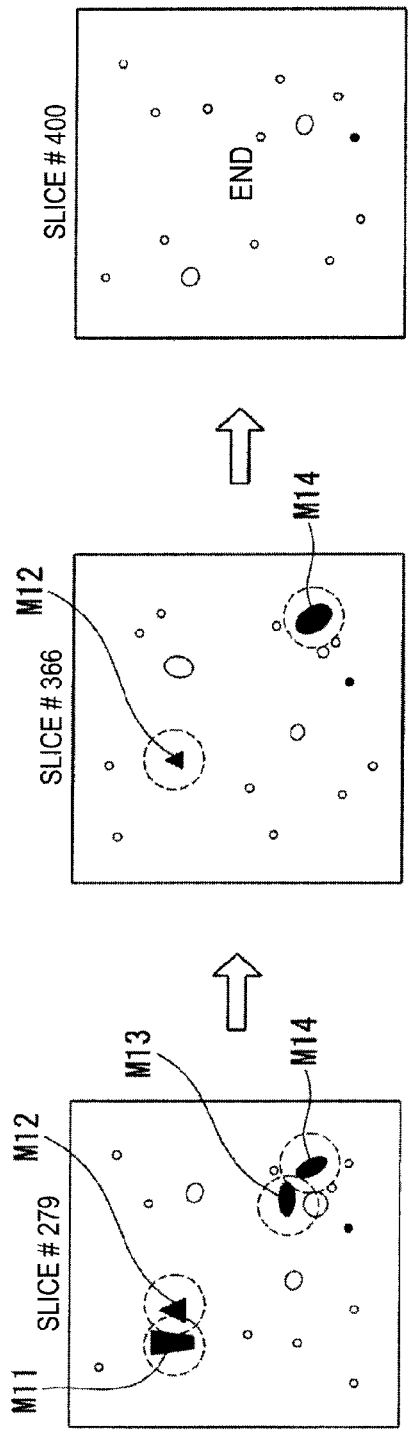
FIGS. 9A and 9B are diagrams illustrating the cross-section processing-and-observation method according to the first embodiment.
Figure 9B:
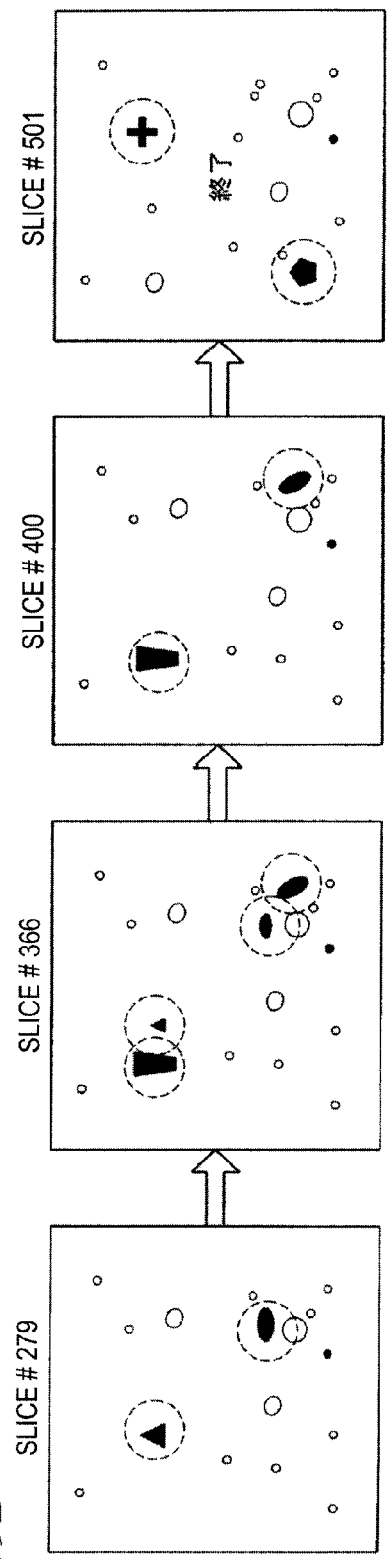

FIGS. 9A and 9B illustrate setting examples of an end condition of the cross-section exposure step. For example, in an example illustrated in FIG. 9A, the end condition of the cross-section exposure step is a position where all the preset specific observation targets (specific materials) M11 to M14 are not detected anymore. In this setting example, the specific examples M11 to M14 are detected based on the EDS map, the EBSD map, the contrast of the SEM image, and the like, and the cross-section exposure step ends at a slicing position where all the specific materials M11 to M14 are not detected anymore in a cross-section.

In addition, in an example illustrated in FIG. 9B, plural types of specific observation targets (specific materials) are set, the threshold number of the specific materials detected is set to 4, and the end condition of the cross-section exposure step is a position where the number of the specific materials detected is less than 4 after a slicing position where the number of the specific materials detected is 4 or more. In this setting example, based on the EDS map, the EBSD map, the contrast of the SEM image, and the like, the cross-section exposure step ends at a slicing position where the number of the specific materials detected is less than 4.

In this way, slicing is not performed in the entire preset region, and the cross-section exposure step is ended according to the detection state of the specific material based on the EDS map, the EBSD map, the contrast of the SEM image, and the like. As a result, the desired specific observation target (specific material) can be efficiently observed within a short period of time.

From the observation images of the cross-sections acquired as above, a three-dimensional image is constructed by the three-dimensional image construction unit 37. The three-dimensional image construction unit 37 acquires the plural cross-sectional images accumulating in the observation image storage unit 35 and arranges the plural cross-sectional images to be substantially parallel to each other at an interval corresponding to the slicing interval. At this time, drift correction is performed based on the correction pattern T which is acquired at the same time with the acquisition of the individual observation images. Spaces between the arranged observation images are complemented to construct a three-dimensional image.

The obtained three-dimensional image is constructed based on the observation images of the cross-sections acquired by updating the conditions of the cross-section exposure step and the conditions of the cross-sectional image acquisition step according to the specific materials. In addition, during the cross-section processing and during the construction, drift correction is performed with reference to the correction pattern which is acquired at a high magnification. Therefore, a highly accurate three-dimensional image which is close to the actual shape can be obtained. Accordingly, a three-dimensional image of a minute defect or structure included in the sample S can be accurately obtained within a short period of time.

Figure 10:
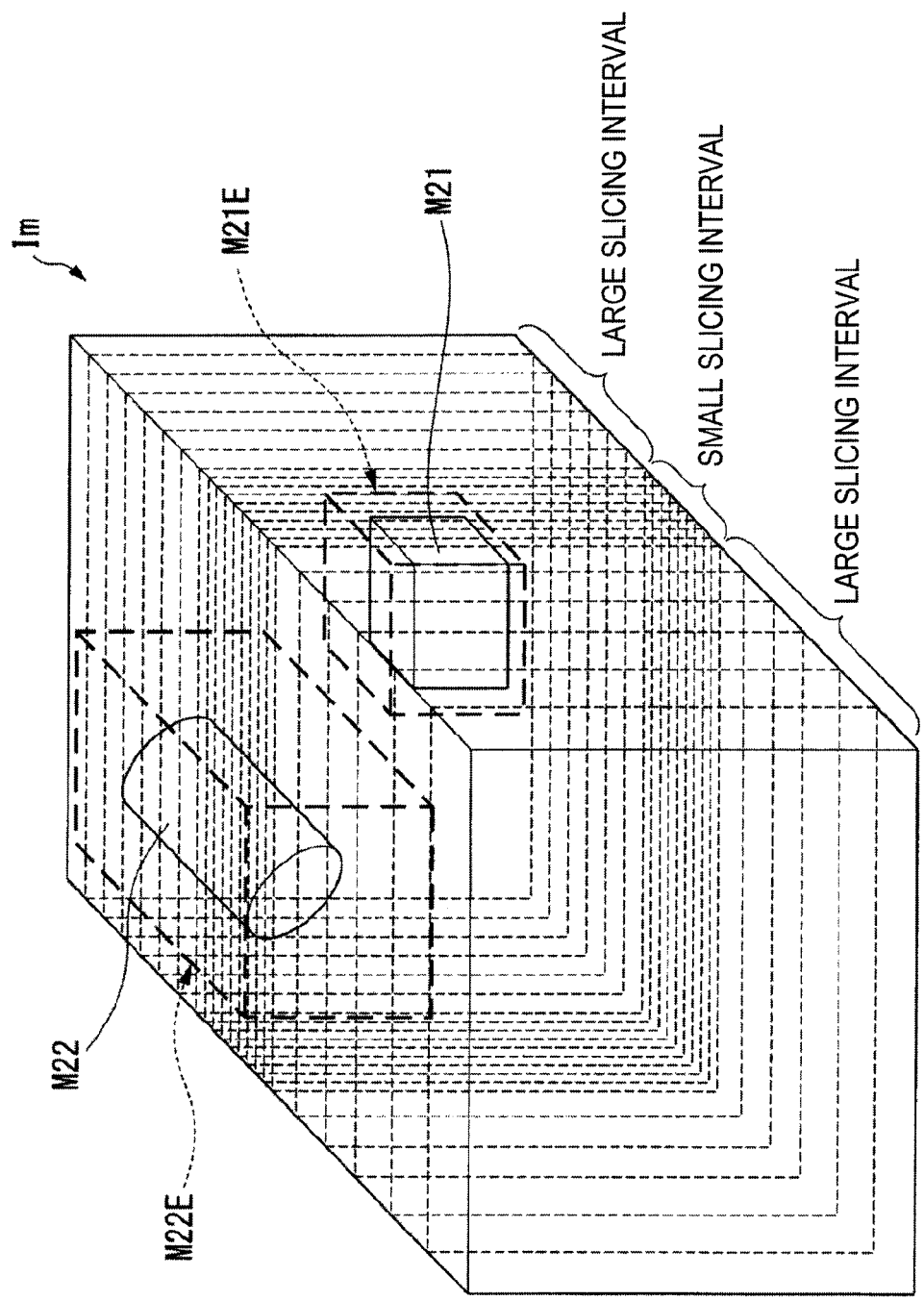
FIG. 10 is a schematic diagram illustrating an example of a three-dimensional image which is constructed using the cross-section processing-and-observation method according to the present invention.

FIG. 10 is illustrates an example of a three-dimensional image which is constructed using the cross-section processing-and-observation method according to the present invention. According to the construction example of the three-dimensional image illustrated in FIG. 10, a sample includes two specific observation targets (specific materials) M21 and M22. Observation images of cross-sections accumulate at a relatively large slicing interval until the specific material M21 is detected. After the specific material M21 is detected, observation images of cross-sections accumulate at a small slicing interval. In addition, an observation image is acquired from a minute region M21E including the specific material M21 with a higher magnification than that of the other regions. Further, a minute region M22E including the specific material M22 is set halfway, and an observation image is also acquired from this region with a high magnification. Cross-section processing ends at a position where the specific material M22 is not detected anymore. In this way, while constructing a highly accurate three-dimensional image Im of the specific materials M21 and M22, the slicing interval of a region including no specific material is increased or slicing ends. As a result, the highly accurate three-dimensional image Im including the specific materials M21 and M22 can be obtained within a short period of time.

(Second Embodiment of Cross-Section Processing-and-Observation Method)

Figure 11:
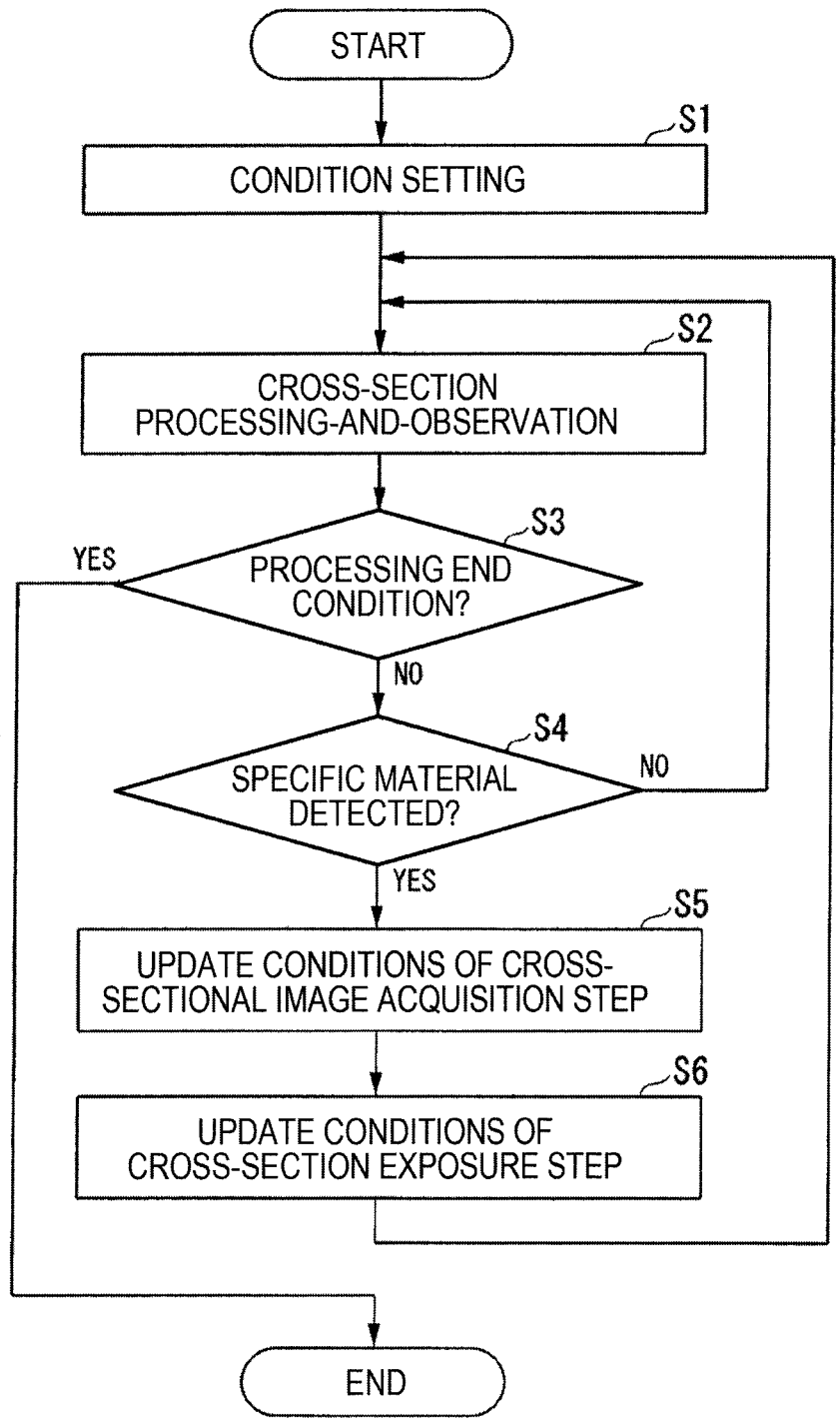
FIG. 11 is a flowchart illustrating a cross-section processing-and-observation method according to a second embodiment of the present invention.

Next, a cross-section processing-and-observation method according to a second embodiment of the present invention will be described in which the cross-section processing-and-observation method according to the first embodiment is automatically performed. FIG. 11 is a flowchart illustrating the cross-section processing-and-observation method. Condition settings of the cross-section processing-and-observation are set (S1). Here, as the condition setting of the cross-section exposure step, initial setting values for an accelerating voltage of the focused ion beam 21, a current value of the focused ion beam 21, an irradiation range of the focused ion beam 21 in the sample S, a visual field range of the focused ion beam 21, and the like are input. In addition, as the condition setting of the cross-sectional image acquisition step, initial setting values for an accelerating voltage of the electron beam 21, a current value of the electron beam 21, an aperture value of an object lens of the electron beam column 12, an astigmatism correction amount, a brightness of an observation image, a contrast, a magnification, an imaging time of the observation image, the number of times of acquiring an observation image for each cross-section, a pixel size, and the like are input. Further, the type of the element included in the specific observation target and the shape of the specific material are input. In addition, an end condition of the cross-section exposure step, for example, the number of the specific materials detected is input. The conditions of the cross-section exposure step and the conditions of the cross-sectional image acquisition step are updated when the specific material is detected after the start of processing.

Next, cross-section processing-and-observation is performed (S2). A preset processing region is irradiated with a focused ion beam, and slicing is performed along a predetermined direction a cross-section formed by slicing is irradiated with an electron beam to acquire an observation image of the cross-section. An X-ray generated from the cross-section is detected by the EDS detector.

Whether or not a processing end condition is satisfied is determined for each cross-section processing-and-observation (S3). The processing end condition is input in advance. For example, as illustrated in FIG. 9, the processing end condition is the slicing position where all the specific materials are not detected anymore or the slicing position where the number of the specific materials detected falls below a predetermined value.

When the cross-section processing-and-observation is continued without ending slicing, the presence of the preset specific material is detected (S4). For example, when the specific material is detected based on the EDS map, the conditions of the cross-sectional image acquisition step are updated (S5). For example, one or plural minute regions including the specific materials may be set for each cross-section. Different observation magnifications, observation ranges, composition analysis settings, and the like are set for the individual minute regions.

Next, the conditions of the cross-section exposure step are updated (S6). For example, according to the update of the conditions of the cross-sectional image acquisition step, a setting of limiting the slicing region to be reduced according to the individual minute regions or a setting of reducing the slicing interval according to the size of the specific material is set.

The cross-section processing-and-observation is repeatedly performed while reflecting the update of the conditions of the cross-sectional image acquisition step and the update of the conditions of the cross-section exposure step (S2). When it is determined that the processing end condition is satisfied, the cross-section processing-and-observation ends at this time.

As described above, by automatically performing the cross-section processing-and-observation method according to the first embodiment based on the previously input setting values, observation images of desired cross-sections or a three-dimensional image constructed based on the observation images can be efficiently and accurately acquired. This control is performed by, for example, the controller 25 illustrated in FIG. 1.

Hereinafter, the cross-section processing-and-observation apparatus and the cross-section processing-and-observation method according to the present invention have been described in detail. However, the present invention is not limited to the above-described embodiments unless specified otherwise.

For example, the conditions of the cross-section exposure step include all the condition settings of the cross-section processing-and-observation apparatus which are necessary to arbitrarily update the slicing interval and the slicing range of the sample. In addition, the conditions of the cross-sectional image acquisition step include all the condition settings of the cross-section processing-and-observation apparatus which are necessary to arbitrarily update the range of an observation image of a cross-section, the number of minute regions set, the magnification of an observation image, and the like.

In addition, as an example of a detection method of the specific observation target (specific material), EDS is mainly used. However, in addition to EDS, various detection methods such as EBSD, a method of detecting a contrast change by an SEM image, and a method of detecting a difference from a comparison with a reference image can be adopted, and the detection method is not particularly limited.

In addition, the detection of the specific observation target is not limited to the detection of the element. As the specific observation target, a molecular structure, a crystal structure, an external shape, or the like can be detected.

What is claimed is:

1. A cross-section processing-and-observation method comprising:
    a cross-section exposure step of irradiating a sample with a focused ion beam to expose a cross-section of the sample;
    a cross-sectional image acquisition step of irradiating the cross-section with an electron beam to acquire a cross-sectional image of the cross-section;
    a step of repeatedly performing the cross-section exposure step and the cross-sectional image acquisition step along a predetermined direction of the sample at a setting interval to acquire a plurality of cross-sectional images of the sample; and
    a specific observation target detection step of detecting a predetermined specific observation target from the cross-sectional image acquired at the cross-sectional image acquisition step;
    wherein in the specific observation target detection step, after a predetermined specific observation target is detected, the setting interval of the cross-section exposure step is set to be shorter than that before the specific observation target is detected.

2. The cross-section processing-and-observation method according to claim 1, wherein the setting interval is equal to or an integer multiple of a pixel size of the cross-sectional image, or the pixel size is an integer multiple of the setting interval.

3. The cross-section processing-and-observation method according to claim 1, wherein
    plural types of the specific observation targets are set, and different condition setting of the cross-section exposure step and different condition setting of the cross-sectional image acquisition step are set for individual regions where the respective specific observation targets are detected.

4. The cross-section processing-and-observation method according to claim 3, wherein when the condition setting of the cross-section exposure step and the condition setting of the cross-sectional image acquisition step are set, the setting interval is equal to or an integer multiple of a pixel size of the cross-sectional image.

5. The cross-section processing-and-observation method according to claim 1, wherein in the specific observation target detection step, an EDS measurement or an EBSD measurement of the cross-section is performed.

6. The cross-section processing-and-observation method according to claim 1, wherein the specific observation target detection step includes observing a contrast change of a cross-sectional image obtained in the cross-sectional image acquisition step.

7. The cross-section processing-and-observation method according to claim 3, wherein the condition setting of the cross-section exposure step includes at least one of an accelerating voltage of the focused ion beam, a current value of the focused ion beam, an irradiation range of the focused ion beam in the sample, and a visual field range of the focused ion beam.

8. The cross-section processing-and-observation method according to claim 1, wherein the specific observation target detection step is performed once while the cross-sectional image acquisition step is performed multiple times.

9. The cross-section processing-and-observation method according to claim 1, wherein in the specific observation target detection step performed after the specific observation target is detected, cross-section processing-and-observation is not performed on other portions of the sample when the specific observation target is not detected anymore.

10. The cross-section processing-and-observation method according to claim 1, further comprising a step of forming a correction mark by irradiation of the focused ion beam,
wherein in the cross-section exposure step, an image of the correction mark is acquired with a higher magnification than a visual field range of the focused ion beam among the conditions of the cross-section exposure step.

11. The cross-section processing-and-observation method according to claim 1, further comprising a step of forming a correction mark by irradiation of the focused ion beam,
wherein in the cross-sectional image acquisition step, when the cross-sectional image is acquired, an image of the correction mark is acquired at the same time with a higher magnification than the magnification of a cross-section observation region observed by the electron beam.

12. A cross-section processing-and-observation apparatus comprising:
a sample stage on which a sample is to be placed;
a focused ion beam column configured to irradiate the sample with a focused ion beam;
an electron beam column configured to irradiate the sample with an electron beam;
one of a secondary electron detector and a backscattered electron detector configured to detect one of secondary electrons and backscattered electrons generated from the sample; and
a control unit configured to repeatedly perform a cross-section exposure step in which the sample is irradiated with a focused ion beam emitted from the focused ion beam column to expose a cross-section of the sample, and a cross-sectional image acquisition step in which the cross-section is irradiated with an electron beam emitted from the electron beam column to acquire a cross-sectional image of the cross-section along a predetermined direction of the sample at a setting interval;
wherein the control unit is further configured to periodically perform a specific observation target detection step of detecting a predetermined specific observation target from the cross-sectional image acquired at the cross-sectional image acquisition step; and
wherein in the specific observation target detection step, after a predetermined specific observation target is detected, the setting interval of the cross-section exposure step is set to be shorter than that before the specific observation target is detected.

13. The cross-section processing-and-observation apparatus according to claim 12, wherein the control unit controls the setting interval to be equal to or an integer multiple of a pixel size of the cross-sectional image or controls the pixel size to be an integer multiple of the setting interval.

* * * * *